United States Patent
Chassot et al.

(10) Patent No.: US 6,811,573 B2
(45) Date of Patent: Nov. 2, 2004

(54) DYES FOR KERATIN FIBRES CONTAINING 1,3-DIAMINO-4-HETEROARYLBENZENE DERIVATIVES AND NOVEL 1,3-DIAMINO-4-HETEROARYLBENZENE DERIVATIVES

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 197 days.

(21) Appl. No.: 10/169,120

(22) PCT Filed: Sep. 10, 2001

(86) PCT No.: PCT/EP01/10411

§ 371 (c)(1),
(2), (4) Date: Jun. 26, 2002

(87) PCT Pub. No.: WO02/062783

PCT Pub. Date: Aug. 15, 2002

(65) Prior Publication Data

US 2003/0093867 A1 May 22, 2003

(30) Foreign Application Priority Data

Feb. 2, 2001 (DE) .......................................... 101 04 768

(51) Int. Cl.[7] ................................................ A61K 7/13
(52) U.S. Cl. ................... 8/405; 8/408; 8/410; 8/411; 8/412; 8/416; 8/423; 8/574; 8/577; 548/563; 548/577; 549/200
(58) Field of Search ........................... 8/405, 408, 410, 8/411, 412, 416, 423, 574, 577; 548/563, 577; 549/200

(56) References Cited

U.S. PATENT DOCUMENTS 4,324,553 A    4/1982   Bugaut et al. ................. 8/407

6,132,475 A  * 10/2000   Chassot et al. ................. 8/409

FOREIGN PATENT DOCUMENTS

| DE | 30 28 131 | 2/1981 |
| DE | 31 32 885 A | 3/1983 |
| EP | 0 272 650 A | 6/1988 |
| EP | 0 667 143 A | 8/1995 |

OTHER PUBLICATIONS

Gonzalez, V., et al: "Complexation Equilibriums and . . . " Quim. Anal. (Barcerlona), 1986, p. 335.

* cited by examiner

Primary Examiner—Yogendra N. Gupta
Assistant Examiner—Eisa Elhilo
(74) Attorney, Agent, or Firm—Michael J. Striker

(57) ABSTRACT

Colorants for keratin fibers containing 1,3-diamino-4-heteroarylbenzene derivatives of general formula (I) or the physiologically tolerated salts thereof

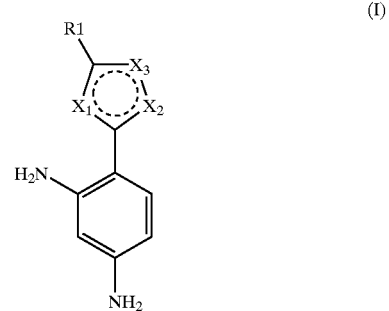

as well as novel 1,3-diamino-4-heteroarylbenzene derivatives.

11 Claims, No Drawings

DYES FOR KERATIN FIBRES CONTAINING 1,3-DIAMINO-4-HETEROARYLBENZENE DERIVATIVES AND NOVEL 1,3-DIAMINO-4-HETEROARYLBENZENE DERIVATIVES

The invention relates to agents for oxidative dyeing of keratin fibers, particularly human hair, based on a developer/coupler combination containing as the coupler a 1,3-diamino-4-heteroarylbenzene derivative, as well as to novel 1,3-diamino-4-heteroarylbenzene derivatives.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diamino-1-(2'-hydroxyethyl)pyrazole and suitable couplers are, for example, resorcinol, 2-aminoresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals such colorations must remain stable over a period of at least 4 to 6 weeks. Moreover, by combining appropriate developers and couplers, it must be possible to create a wide range of different color shades.

Attempts have already been made to improve the properties of m-phenylenediamines by introduction of substituents. In this respect, the reader is referred to German Unexamined Patent Application DE-OS 30 28 131 which, among other things, describes colorants containing as couplers special m-phenylenediamines alkyl-substituted in the 4-position.

The hitherto known colorants, however, do not fully meet all requirements placed on colorants. Hence, a need continued to exist for novel couplers capable of meeting the aforecited requirement to a major extent.

We have now found that by use of 1,3-diamino-4-heteroarylbenzene derivatives of general formula (I) it is possible to achieve intense, stable blue color shades in addition to natural, purple or violet ones.

Hence, the object of the present invention is an agent for oxidative dyeing of keratin fibers, for example wool, furs, feathers or hair, particularly human hair, based on a developer/coupler combination containing as the coupler at least one 1,3-diamino-4-heteroarylbenzene derivative of formula (I) or a physiologically tolerated salt thereof,

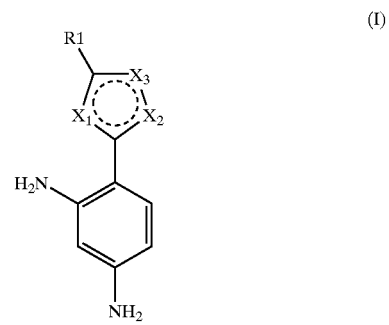

wherein

X1 denotes sulfur, oxygen, C—R3 or N—R2;

X2 denotes nitrogen or C—R4;

X3 denotes sulfur, nitrogen, oxygen, CR—5 or N—R2;

R1, R3, R4 and R5 can be equal or different and independently of each other denote hydrogen, a halogen atom (fluorine, chlorine, bromine or iodine), a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-monoalkylamino group, a di($C_1$–$C_4$)alkylamino group, a di($C_1$–$C_4$-hydroxyalkyl)amino group, a $C_1$–$C_4$-hydroxyalkylamino group, a trifluoromethane group, a —C(O)CH$_3$ group, a —C(O)CF$_3$ group, an —Si(CH$_3$)$_3$ group, a $C_1$–$C_4$-hydroxyalkyl group or a $C_3$–$C_4$-dihydroxyalkyl group;

R2 denotes hydrogen, a $C_1$–$C_6$-alkyl group, a $C_2$–$C_4$-hydroxyalkyl group, a phenyl group or an acetyl group;

wherein at least one and at the most two X1 to X3 groups denote C—R3, or C—R4 or C—R5, and at the most one of the X1 to X3 groups denotes sulfur, oxygen or N—R2.

Compounds of formula (I) are, for example:

1,3-diamino-4-(2-thiophenyl)benzene, 1,3-diamino-4-(3-thiophenyl)benzene, 1,3-diamino-4-(1-methyl-1H-2-pyrrolyl)benzene, 1,3-diamino-4-(2-pyrrolyl)benzene, 1,3-diamino-4-(2-furyl)benzene, 1,3-diamino-4-(2-thiazolyl)benzene, 1,3-diamino-4-(1H-2-imidazolyl)benzene, 1,3-diamino-4-(3-furyl)benzene, 1,3-diamino-4-(3-amino-2-thiophenyl)benzene, 1,3-diamino-4-(3-chloro-2-thiophenyl)benzene, 1,3-diamino-4-(3-methyl-2-thiophenyl)benzene, 1,3-diamino-4-(3-nitro-2-thiophenyl)-benzene, 1,3-diamino-4-(4-amino-2-thiophenyl)benzene, 1,3-diamino-4-(4-chloro-2-thiophenyl)benzene, 1,3-diamino-4-(4-methyl-2-thiophenyl)benzene, 1,3-diamino-4-(4-nitro-2-thiophenyl)benzene, 1,3-diamino-4-(5-amino-2-thiophenyl)benzene, 1,3-diamino-4-(5-chloro-2-thiophenyl)benzene, 1,3-diamino-4-(5-methyl-2-thiophenyl)benzene, 1,3-diamino-4-(5-nitro-2-thiophenyl)benzene, 1,3-diamino-(2-amino-3-thiophenyl)benzene, 1,3-diamino-(2-chloro-3-thiophenyl)benzene, 1,3-diamino-(2-methyl-3-thiophenyl)benzene, 1,3-diamino-(2-nitro-3-thiophenyl)benzene, 1,3-diamino-(4-amino-3- thiophenyl)benzene, 1,3-diamino-(4-chloro-3-thiophenyl)benzene, 1,3-diamino-(4-methyl-3-thiophenyl)benzene, 1,3-diamino-(4-nitro-3-thiophenyl)benzene, 1,3-diamino-(5-amino-3-thiophenyl)benzene, 1,3-diamino-(5-chloro-3-thiophenyl)benzene, 1,3-diamino-(5-methyl-3-thiophenyl)benzene and 1,3-diamino-(5-nitro-3-thiophenyl)benzene.

Preferred compounds of formula (I) are those wherein (i) X1 or X3 denotes sulfur, X2 denotes C—R4 and X3 denotes C—R5 or X1 denotes C—R3; or (ii) X1 or X3 stands for sulfur, X2 stands for C—R4 and X3 stands for C—R5 or X1 stands for C—R3, and at least two of the R1, R3, R4 and R5 groups denote hydrogen.

Particularly preferred are the following 1,3-diamino-4-heteroarylbenzene derivatives: 1,3-diamino-4-(2-thiophenyl)benzene, 1,3-diamino-4-(3-thiophenyl)benzene and the physiologically tolerated salts thereof.

The compounds of formula (I) can be used as free bases or in the form of their physiologically tolerated salts with inorganic or organic acids, for example hydrochloric acid, sulfuric acid, phosphoric acid, acetic acid, propionic acid, lactic acid or citric acid.

The 1,3-diamino-4-heteroarylbenzene derivatives of formula (I) are contained in the colorant of the invention in a total amount of about 0.005 to 20 wt. %, an amount of about 0.01 to 5 wt. % and particularly 0.1 to 2.5 wt. % being preferred.

Suitable developers are all developers known to be used for such colorants, for example 1,4-diaminobenzene (p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(2-thiophenyl)benzene, 1,4-diamino-2-(3-thiophenyl)benzene, 1,4-diamino-2-(3-pyridinyl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 1-(2,5-diaminophenyl)-ethanol, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)-amino]-2-methylaniline, 4-[(2-methoxyethyl)amino]aniline, 4-[(3-hydroxypropyl)amino]-aniline, 4-[(2,3-dihydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-amino-phenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl) amino]methylphenol, 4-amino-2-methylphenol, 4-amino-2-methoxymethyl)phenol, 4-amino-2-(2-hydroxyethyl) phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl) methyl]-4,5-diamino-1H-pyrazole, 4,5-diamino-1-methyl-1H-pyrazole, 4,5-diamino-3-methyl-1-methyl-1H-pyrazole, 2-aminophenol, 2-amino-6-methylphenol and 2-amino-5-methylphenol.

The colorant of the invention can optionally also contain other couplers, for example 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-[(2-hydroxyethyl) amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-di[(2-hydroxyethyl)amino]aniline, 4-amino-2-di[(2-hydroxyethyl)amino]-1-ethoxybenzene, 5-methyl-2-(1-methylethyl)phenol, 3-[(2-hyd roxyethyl)amino]aniline, 3-[(2-aminoethyl)amino]aniline, 1,3-di(2,4-diaminophenoxy)propane, 1,3-di(2,4-diaminophenoxy) methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl) amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxynaphthalene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5, 6-dihydroxyindole, 5, 6-dihydroxyindoline, 5-hydroxyindole, 6-hydroxyindole, 7-hydroxyindole and 2,3-indolinedione.

The couplers and developers can be present in the colorant of the invention either individually or in admixture with one another, the total amount of couplers and developers in the colorant of the invention each being about 0.005 to 20 wt. % preferably about 0.01 to 5.0 wt. % and particularly 0.1 to 2.5 wt. % (based on the total amount of colorant). The total amount of the developer-coupler combination contained in the colorant described herein is preferably about 0.01 to 20 wt. %, an amount of about 0.02 to 10 wt. % and especially 0.2 to 6 wt. % being particularly preferred. In general, the developer and the coupler are used in approximately equimolar amounts; however, it is not disadvantageous if the developer is present in a certain excess or deficiency (for example in a coupler: developer ratio of 1:2 to 1:0.5).

Moreover, the colorant of the invention can also contain other dye components, for example 6-amino-2- methylphenol and 2-amino-5-methylphenol, as well as common anionic, cationic, zwitterionic or nonionic direct dyes, for example triphenylmethane dyes such as 4-[(4'-aminophenyl)-(4'-imino-2", 5"-cyclohexadien-1 "-ylidene) methyl]-2-methylaminobenzene monohydrochloride (Color Index [C.I.] 42 510) and 4-[(4'-amino-3'-mthylphenyl)-(4"-imino-3"-methyl-2",5"-cyclohexadien-1"-ylidene) methyl]-2-methylarninobenzene monohydrochloride (C.I. 42 520), aromatic nitro dyes such as 4-(2'-hydroxyethyl) aminonitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl-2-nitroaniline, 5-chloro-2-hydroxy-4-nitroaniline, 2-amino-4-chloro-6-nitrophenol and 1-(2'ureidoethyl)amino-4-nitrobenzene, azo dyes such as, for example, sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain the aforesaid dye components in an amount from about 0.1 to 4 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenolates.

Moreover, if the colorants of the invention are to be used for coloring hair, they can contain other common cosmetic agents, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents, such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5 wt. %.

Depending on the composition, the colorant of the invention can be weakly acidic, neutral or alkaline. In particular, it has a pH of about 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorants are mixed with an oxidant just before use, and the resulting mixture is applied to hair in an amount sufficient for the hair-dyeing treatment, in general about 50 to 200 grams, depending on the hair fullness. The ready-to-use oxidation dye obtained by mixing with the oxidant preferably has a pH of 6.5 to 11.5.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 1,3-diamino-4-heteroarylbenzenederivative of formula (I) as coupler give hair colorations of excellent color fastness, particularly in terms of light fastness, wash fastness and rubbing fastness. As far as the dyeing properties are concerned, the hair colorants of the invention, depending on the kind and composition of the dye component, provide a wide range of different color shades from blond to brown, purple, violet and even blue and black, depending on the developer-coupler combination. The intense, stable blue color shades obtainable in this manner are particularly noteworthy. In particular, the very good coloring properties of the hair colorant of the present invention also manifest themselves in that these colorants make it possible to dye graying hair, chemically not previously damaged, without any problems and with good covering power.

The 1,3-diamino-4-heteroarylbenzene derivatives of formula (I) can be prepared by known methods of synthesis, for example by methods similar to those described in the following examples.

The 1,3-diamino-4-heteroarylbenzene derivatives of formula (I) are readily water-soluble and afford colorations, particularly in the blue range of shades, with excellent color fastness, particularly in terms of light fastness, wash fastness and rubbing fastness. Moreover, they have outstanding storage stability, particularly as constituents of the hereindescribed oxidation colorants.

Hence, another object of the present invention are 1,3-diamino-4-heteroarylbenzene derivatives of general formula (I) wherein X2 is not nitrogen when X1 denotes sulfur.

The following examples illustrate the object of the invention in greater detail without limiting its scope.

EXAMPLES

Example 1

A. Synthesis of tert.butyl (4-bromo-3-tert.butoxycarbonylaminophenyl)carbamate

A solution of 6.0 g (33.7 mmoles) of N-bromosuccinimide in 50 mL of 1,2-dimethoxyethane was added dropwise to a suspension of 10 g (32.4 mmoles) of tert.butyl (3-tert.butoxycarbonylaminophenyl)carbamate at 0° C. over a period of 2 hours. The reaction mixture was allowed to agitate for an additional 2 hours. At the end of the reaction, the reaction mixture was poured into 300 mL of water, which produced a precipitate. The precipitate was filtered off and washed with water.

This gave 11 g (94% of the theoretical) of tert.butyl (4-bromo-3-tert.butoxycarbonylaminophenyl)carbamate.

$^1$H-NMR (300 MHz, DMSO-D6: δ=9.51 (s,1H), 8.43 (s, 1H), 7.89 (s, 1H), 7.47 (d, 1H), 7.18 (d, 1H), 1.47 (d, 18H).

B. Synthesis of tert.butyl 3-tert.butoxycarbonylamino-4-(4,4,5,5-tetramethyl -[1,3,2]dioxa-2-borolanyl)phenyl Carbamate 210 mL of degassed dioxane was added to a mixture of 7.8 g (20.2 mmoles) of tert.butyl (4-bromo-3-tert.butoxycarbonylaminophenyl)carbamate from step A, 12.8 g (50.6 mmoles) of 4,4,4',4',5,5,5',5'-octamethyl[2,2'] bis([1,3,2]dioxaborinanyl), 2 g (2.9 mmoles) of dichloro-[1,1'-bis(diphenylphospino)ferrocene]palladium[(PdCl$_2$ (dppf)] and 6.2 g (63.2 mmoles) of potassium acetate under argon. The mixture was allowed to agitate 26 h at 80° C., and to it was then added a mixture of 4.2 g (16.9 mmoles) of diboronpinacole ester and 700 mg (0.95 mmole) of PdCl$_2$ (dppf). The reaction mixture was allowed to agitate for an additional 14 h at 80° C., after which it was poured into water and the resulting mixture was extracted with ethyl acetate. The organic phase was then washed with saturated aqueous sodium chloride solution, dried over sodium sulfate, filtered and the filtrate evaporated to dryness. The resulting crude product was purified on deactivated silicate gel with hexane/ethyl acetate (1:1). This gave 6.20 g (71% of the theoretical) of tert.butyl 3-tert.butoxycarbonylamino-4-(4,4,5,5-tetramethyl[1,3,2]dioxa-2-borolanyl) phenylcarbamate.

C. Synthesis of 4-heteroaryl-1,3-diaminobenzenes 0.09 g (0.0002 mole) of tert.butyl 3-tert.butoxycarbonylamino-4-(4,4,5,5-tetramethyl[,3,2] dioxa-2-borolanyl)phenyl carbamate from step B and 0.0004 mole of the appropriate bromo derivative were dissolved in 10 mL of 1,2-dimethoxyethane. Then, 0.01 g (0.000005 mole) of tetrakis-(triphenylphosphine)palladiumand 0.26 mL of 2N potassium carbonate solution were added, and the reaction mixture was heated to 80° C. At the end of the reaction, the reaction mixture was poured into 10 mL of ethyl acetate and the organic phase was extracted with dilute sodium hydroxide solution and then dried over magnesium sulfate. The solvent was distilled off in a rotary evaporator, and the residue was purified on silica gel with petroleum ether/ethyl acetate (9:1). The product thus obtained was dissolved in 4 mL of ethanol and heated to 50° C. To prepare the hydrochloride, 1.5 mL of a 2.9 molar ethanolic solution of hydrochloric acid was added dropwise. The precipitate was filtered off, washed twice with 1-mL portions of ethanol and then dried.

a) 1,3-Diamino-4-(2-thiophenyl)benzene Hydrochloride
   Bromo derivative used: 2-bromothiophene
   Mass spectrum: MH+191(50)
b) 1,3-Diamino-4-(3-methyl-2-thiophenyl)benzene Hydrochloride
   Bromo derivative used: 2-bromo-3-methylthiophene
   Mass spectrum: MH+205(80)
c) 1,3-Diamino-4-(5-nitro-2-thiophenyl)benzene Hydrochloride
   Bromo derivative used: 2-bromo-5-nitrothiophene
   Mass spectrum: MH+236(100)
d) 1,3-Diamino-4-(2-thiazolyl)benzene
   Bromo derivative used: 2-bromothiazole
   Mass spectrum: MH+192(100)

Examples 2 to 5

Hair Colorants

Hair colorant solutions having the following composition were prepared:

| | |
|---|---|
| 1.25 mmoles | of coupler of formula (I) according to Table 1 |
| 1.25 mmoles | of developer according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Developer* | | | |
|---|---|---|---|---|---|
| Example No. | Coupler of Formula(I) as per | I 1,4-di-amino-benzene | II 2,5-di-amino-toluene sulfate | III 2,5-di-amino-phenyl-ethanol sulfate | IV 4,5-diamino-1-(2'-hy-droxyethyl)-pyrazole sulfate |
| 2. | Example 1a | dark-blue | dark-blue | dark-blue | purple |
| 3. | Example 1b | dark-blue | dark-blue | dark-blue | purple |
| 4. | Example 1c | dark-blue | dark-blue | dark-blue | purple |
| 5. | Example 1d | gray | light-gray | light-gray | light-gray |

*The original reads "Coupler" - an abvious error - Translator

Examples 6 to 11

Hair Colorants

Hair colorant solutions of the following composition were prepared:

| | |
|---|---|
| X g | of 1,3-diamino-4-heteroarylbenzene (coupler K1 of formula (I) as per Table 4) |
| U g | of developer E8 to E15 as per Table 2 |
| Y g | of coupler K11 to K36 as per Table 4 |
| Z g | of direct dye D1 to D3 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. The coloring results are presented in Table 5.

TABLE 2

Developers

| | |
|---|---|
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

Direct Dyes

| | |
|---|---|
| D1 | 2,6-diamino-3-[(3-pyridinyl)azo]pyridine |
| D2 | 6-chloro-2-ethylamino-4-nitrophenol |
| D3 | 2-amino-6-chloro-4-nitrophenol |

TABLE 4

Couplers

| | |
|---|---|
| K1 | 1,3-diamino-4-(2-thiophenyl)benzene hydrochloride |
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene.HCl |
| K35 | 3,4-methylenedioxyphenol |
| K36 | 2-amino-5-methylphenol |

TABLE 5

Hair Colorants

| Dyes | Example No. | | | | | |
|---|---|---|---|---|---|---|
| | 6 | 7 | 8 | 9 | 10 | 11 |
| | (Amount of dye in grams) | | | | | |
| K1 | 0.1 | 0.12 | 0.05 | 0.07 | 0.10 | 0.12 |
| E8 | 0.30 | | | | | |
| E9 | | | | | 0.25 | 0.3 |
| E15 | | 0.25 | 0.3 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring result | blond | blond | blond | blond | blond | blond |

Examples 13 to 17

Hair Colorants

Dye carriers in cream form and having the following composition were prepared:

| | |
|---|---|
| X g | of 1,3-diamino-4-heteroarylbenzene (coupler K1 of formula (I) as per Table 4) |
| U g | of developer E8 to E15 as per Table 2 |
| Y g | of coupler K11 to K36 as per Table 4 |
| Z g | of direct dye D2 as per Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Just before use, 30 g of the foregoing coloring cream was mixed with 30 g of a 6% aqueous solution of hydrogen peroxide. The mixture was then applied to the hair. After an exposure time of 30 min at 40° C., the hair was rinsed with water, washed with a commercial shampoo and dried. The coloring results are shown in Table 6.

TABLE 6

Hair Colorants

| Dyes | Example No. | | | | | |
|---|---|---|---|---|---|---|
| | 12 | 13 | 14 | 15 | 16 | 17 |
| | (Amount of dye in grams) | | | | | |
| K1 | 0.6 | 1.3 | 1.15 | 0.15 | 0.15 | 0.15 |
| E8 | 1.5 | | | | | |
| E13 | | 1.6 | | | | 0.7 |
| E15 | | | 1.8 | 0.7 | 0.7 | |
| K12 | 0.6 | | | | | |
| K31 | 1.10 | 1.10 | 1.10 | 0.40 | 0.40 | 0.40 |
| K23 | | | 0.05 | 0.10 | 0.10 | 0.10 |
| D2 | | | | 0.10 | 0.10 | 0.10 |
| Coloring results | black | black | black | brown | brown | brown |

Unless otherwise indicated, all percentages in the present application are by weight.

What is claimed is:

1. Agent for oxidative dyeing of keratin fibers containing a combination of at least one coupler and at least one developer, wherein said at least one coupler comprises at least one 1,3-diamino-4-heteroarylbenzene derivative of formula (I) or a physiologically tolerated salt thereof,

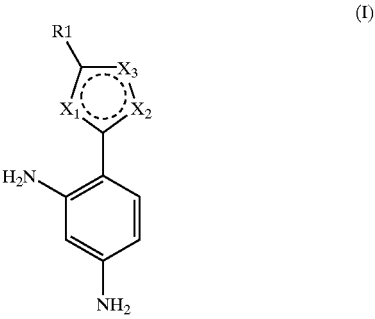

wherein

X1 denotes sulfur, oxygen, C—R3 or N—R2;

X2 denotes nitrogen or C—R4;

X3 denotes sulfur, nitrogen, oxygen, C—R5 or N—R2;

R1, R3, R4 and R5 can be equal or different and independently of each other denote hydrogen, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-monoalkylamino group, a di($C_1$–$C_4$)-alkylamino group, a di($C_1$–$C_4$-hydroxyalkyl)amino group, a $C_1$–$C_4$-hydroxyalkylamino group, trifluoromethane group, a —C(O)CH$_3$ group, a —C(O)CF$_3$ group, an —Si(CH$_3$)$_3$ group, a $C_1$–$C_4$-hydroxyalkyl group or a $C_3$–$C_4$-dihydroxyalkyl group;

R2 denotes hydrogen, a $C_1$–$C_6$-alkyl group, a $C_2$–$C_4$-hydroxyalkyl group, a phenyl group or an acetyl group;

wherein at least one and at the most two X1 to X3 groups denote C—R3, or C—R4 or C—R5, and at the most one of the X1 to X3 groups denotes sulfur, oxygen or N—R2.

2. Agent according to claim 1, wherein X1 or X3 denotes sulfur, X2 denotes C—R4 and X3 denotes C—R5 or X1 denotes C—R3.

3. Agent according to claim 1, wherein X1 or X3 denote sulfur, X2 denotes C—R4 and X3 denotes C—R5 or X1 denotes C—R3, and at least two of the R1, R3, R4 and R5 groups are hydrogen.

4. Agent according to claim 1, wherein at at least one 1,3-diamino-4-heteroarylbenzene derivative of formula (I) is selected from the group consisting of 1,3-diamino-4-(2-thiophenyl)benzene, 1,3-diamino-4-(3-thiopheny)benzene and the physiologically tolerated salts thereof.

5. Agent according to claim 1, containing the at least one 1,3-diamino-4-heteroarylbenzene of formula (I) in an amount from 0.005 to 20 wt. %.

6. Agent according to claim 1, having a pH from 6.5 to 11.5.

7. Agent according to claim 1, wherein the at least one developer is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(2-thio-phenyl)-benzene, 1,4-diamino-2-(3-thio-phenyl)benzene, 1,4-diamino-2-(3-pyridinyl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 1-(2,5-diaminophenyl)-ethanol, 2-[2-(acetylamino)ethoxy]-1,4-diamino-benzene, 4-phenyl-amino-aniline, 4-dimethylamino-aniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]-aniline, 4-[(2,3-dihydroxypropyl)amino]aniline, 1,4-diamino-2-(2-hydroxyethyl)-benzene, 1,4-diamino-2-(1-methylethyl)benzene, 1,3-bis-[(4-aminophenyl)-(2-hydroxyethyl)amino]-2-propanol, 1,4-bis-[(4-aminophenyl)-amino]butane, 1,8-bis(2,5-diaminophenoxy)-3,6-dioxaoctane, 4-amino-phenol, 4-amino-3-methylphenol, 4-amino-3-(hydroxymethyl)phenol, 4-amino-3-fluorophenol, 4-methyl-aminophenol, 4-amino-2-(aminomethyl)phenol, 4-amino-2-(hydroxymethyl)phenol, 4-amino-2-fluorophenol, 4-amino-2-[(2-hydroxyethyl)amino]-methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-methyl-1H-pyrazole, 2-aminophenol, 2-amino-6-methylphenol and 2-amino-5-methyl-phenol.

8. Agent according to claim 1, wherein the at least one developer and the at least one coupler are each present in a total amount of 0.005 to 20 wt/%.

9. Agent according to claim 1, further comprising at least one direct dye.

10. Agent according to claim 1, consisting of a hair colorant.

11. A 1,3-diamino-4-heteroarylbenzene derivative at formula (I)

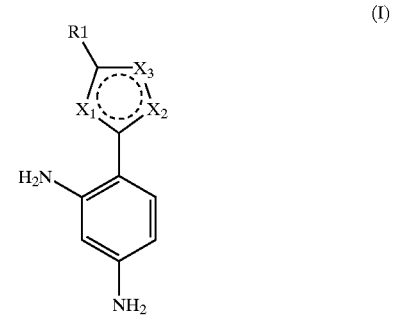

wherein

X1 denotes sulfur, oxygen, C—R3 or N—R2;

X2 denotes nitrogen or C—R4;

X3 denotes sulfur, nitrogen, oxygen, C—R5 or N—R2;

R1, R3, R4 and R5 can be equal or different and, independently of each other, denote hydrogen, a halogen atom, a cyano group, a $C_1$–$C_4$-alkoxy group, a $C_1$–$C_6$-alkyl group, a $C_1$–$C_4$-alkylthloether group, a mercapto group, a nitro group, an amino group, a $C_1$–$C_4$-monoalkylamino group, a di($C_1$–$C_4$)alkylamino group, a di($C_1$–$C_4$-hydroxyalkyl) amino group, a $C_1$–$C_4$-hydroxyalkylamino group, a trifluoromethane group, a —C(O)CH$_3$ group, a —C(O)CF$_3$ group, an —Sl(CH$_3$)$_3$ group, a $C_1$–$C_4$-hydroxyalkyl group or a $C_3$–$C_4$-dihydroxyalkyl group;

R2 denotes hydrogen, a $C_1$–$C_6$-alkyl group, a $C_2$–$C_4$-hydroxyalkyl group, a phenyl group or an acetyl group;

wherein at least one and at the most two X1 to X3 groups denote C—R3, C—R4 or C—R5, and at the most one of the X1 to X3 groups denotes sulfur, oxygen or N—R2, with the proviso that X2 does not stand for nitrogen when X1 stands for sulfur.

* * * * *